United States Patent
Chiang et al.

(10) Patent No.: US 7,874,991 B2
(45) Date of Patent: Jan. 25, 2011

(54) ULTRASOUND 3D IMAGING SYSTEM

(75) Inventors: Alice M. Chiang, Weston, MA (US); Michael Brodsky, Brookline, MA (US); Xingbai He, Andover, MA (US); William M. Wong, Milton, MA (US)

(73) Assignee: Teratech Corporation, Burlington, MA (US)

( * ) Notice: Subject to any disclaimer, the term of this patent is extended or adjusted under 35 U.S.C. 154(b) by 0 days.

(21) Appl. No.: 11/474,098

(22) Filed: Jun. 23, 2006

(65) Prior Publication Data

US 2008/0009739 A1    Jan. 10, 2008

(51) Int. Cl.
*A61B 8/14*    (2006.01)
*A61B 8/00*    (2006.01)

(52) U.S. Cl. .............. 600/459; 600/437; 600/440; 600/441; 600/444; 600/447; 600/453

(58) Field of Classification Search .......... 600/437, 600/440–441, 444, 447, 453, 459, 472
See application file for complete search history.

(56) References Cited

U.S. PATENT DOCUMENTS

| | | | |
|---|---|---|---|
| 5,235,982 A | 8/1993 | O'Donnell | |
| 5,295,485 A | 3/1994 | Shinomura et al. | |
| 5,435,313 A | 7/1995 | Noda et al. | |
| 5,546,807 A | 8/1996 | Oxaal et al. | |
| 5,590,658 A * | 1/1997 | Chiang et al. | 600/447 |
| 5,622,177 A | 4/1997 | Breimesser et al. | |
| 5,817,024 A | 10/1998 | Ogle et al. | |
| 5,893,363 A | 4/1999 | Little et al. | |
| 5,911,692 A | 6/1999 | Hussain et al. | |
| 5,997,479 A | 12/1999 | Savord et al. | |
| 6,106,471 A | 8/2000 | Wiesauer et al. | |
| 6,106,472 A * | 8/2000 | Chiang et al. | 600/447 |
| 6,155,979 A * | 12/2000 | Moser | 600/445 |
| 6,224,556 B1 | 5/2001 | Schwartz et al. | |
| 6,245,017 B1 | 6/2001 | Hashimotot et al. | |
| 6,279,399 B1 | 8/2001 | Holm | |
| 6,292,433 B1 | 9/2001 | Gilbert et al. | |
| 6,375,617 B1 * | 4/2002 | Fraser | 600/443 |
| 6,468,216 B1 | 10/2002 | Powers et al. | |
| 6,482,160 B1 | 11/2002 | Stergiopoulos et al. | |
| 6,491,634 B1 * | 12/2002 | Leavitt et al. | 600/447 |
| 6,497,663 B2 | 12/2002 | Fraser et al. | |
| 6,537,220 B1 | 3/2003 | Friemel et al. | |
| 6,558,325 B1 | 5/2003 | Pang et al. | |
| 6,638,220 B2 | 10/2003 | Satoh | |
| 6,671,227 B2 | 12/2003 | Gilbert et al. | |
| 6,679,847 B1 | 1/2004 | Robinson et al. | |
| 6,709,395 B2 | 3/2004 | Poland | |
| 6,716,174 B1 | 4/2004 | Li | |

(Continued)

FOREIGN PATENT DOCUMENTS

JP    2004/008642    1/2004

*Primary Examiner*—Brian Casler
*Assistant Examiner*—James Kish
(74) *Attorney, Agent, or Firm*—Weingarten, Schurgin, Gagnebin & Lebovici LLP

(57) ABSTRACT

The present invention relates to an ultrasound imaging system in which the scan head either includes a beamformer circuit that performs far field subarray beamforming or includes a sparse array selecting circuit that actuates selected elements. When used with second stage beamforming system, three dimensional ultrasound images can be generated.

24 Claims, 14 Drawing Sheets

U.S. PATENT DOCUMENTS

| | | |
|---|---|---|
| 6,721,235 B2 | 4/2004 | Chiang et al. |
| 6,821,251 B2 | 11/2004 | Alexandru |
| 6,836,159 B2 | 12/2004 | Wodnicki |
| 6,865,140 B2 | 3/2005 | Thomenius et al. |
| 6,869,401 B2 | 3/2005 | Gilbert et al. |
| 6,875,178 B2 | 4/2005 | Phelps et al. |
| 6,890,301 B2 | 5/2005 | Jago et al. |
| 6,967,975 B2 | 11/2005 | Van Stalen et al. |
| 6,974,417 B2 | 12/2005 | Lockwood et al. |
| 6,980,844 B2 | 12/2005 | Schoisswohl |
| 7,115,093 B2 | 10/2006 | Halmann et al. |
| 7,141,020 B2 | 11/2006 | Poland et al. |
| 7,217,243 B2 | 5/2007 | Takeuchi |
| 7,227,813 B2 | 6/2007 | Miller |
| 7,285,094 B2 | 10/2007 | Nohara et al. |
| 7,297,118 B2 | 11/2007 | Kristoffersen |
| 7,322,936 B2 | 1/2008 | Takeuchi |
| 7,527,591 B2 | 5/2009 | Haugen et al. |
| 7,527,592 B2 | 5/2009 | Haugen et al. |
| 2002/0120193 A1 | 8/2002 | Chiang et al. |
| 2003/0216645 A1* | 11/2003 | Yao et al. .................... 600/437 |
| 2005/0057284 A1* | 3/2005 | Wodnicki .................... 327/100 |
| 2005/0113698 A1 | 5/2005 | Kristoffersen et al. |
| 2005/0288588 A1 | 12/2005 | Weber et al. |
| 2006/0058667 A1 | 3/2006 | Lemmerhirt et al. |
| 2006/0064014 A1 | 3/2006 | Falco et al. |
| 2007/0232910 A1 | 10/2007 | Hwang et al. |

* cited by examiner

ULTRASOUND 3D IMAGING SYSTEM

BACKGROUND OF THE INVENTION

Medical ultrasound imaging has become an industry standard for many medical imaging applications. Techniques have been developed to provide three dimensional (3D) images of internal organs and processes using a two dimensional (2D) transducer array. These systems require thousands of beamforming channels. The power required to operate such systems has resulted in the use of an analog phase shift technique with a digital delay beamformer that results in a compromise of image quality.

There is a continuing need for further improvements in ultrasound imaging technologies enabling improved real-time three dimensional imaging capability. In addition, this improved capability should support continuous real-time display for a fourth dimensional 4D function.

SUMMARY OF THE INVENTION

The present invention relates to a system for ultrasound medical imaging that provides three dimensional (3D) imaging using a two dimensional (2D) array of transducer elements in a probe housing. In a preferred embodiment, the probe housing contains a first beamforming circuit that transmits beamformed data to a second housing having a second beamforming circuit. The first beamforming circuit provides a far-field subarray beamforming operation. The resulting beamformed data is transmitted from the scan head to a second housing having the second beamforming circuit that provides near-field beamsteering and beamfocusing.

A preferred embodiment provides a scan head that can be connected to a conventional ultrasound system in which the scan head provides the inputs to the conventional beamforming processing function. The scan head beamformer can utilize a low power charge domain processor having at least 32 beamforming channels.

An alternative preferred embodiment of the invention employs a sparse array where only a fraction of the transducer elements need to be activated. By selecting the four corner elements of the array to provide proper mean lobe bandwidth, minimizing average sidelobe energy and clutter, eliminating periodicity and maximizing peak to side lobe ratio, quality images are produced. To steer the beams across the volume or region of interest, different transducer elements must be actuated in proper sequence to maintain the peak to sidelobe ratio. The system processor can be programmed to provide the desired sequence for transducer actuation to direct the beam at different angles. Alternatively, a discrete controller can be used to control sparse array actuation. A preferred embodiment provides a scan head with integrated switching circuits for sequentially selecting sparse array actuation elements for sequential multiple beamforming. The scan head can be connected to a conventional ultrasound system in which the scan head provides the inputs to the conventional beamforming processing functions.

In addition to the three dimensional (3D) display capability, a fourth dimension or time resolved image display can be used to record and display a sequence of images recorded at 10 frames per second or higher, for example. This enables viewing of rapidly changing features such as blood or fluid flow; heart wall movement etc. at video frames rates of 30 frames per second.

DETAILED DESCRIPTION OF THE INVENTION

The objective of the beamforming system is to focus signals received from an image point onto a transducer array. By inserting proper delays in a beamformer to wavefronts that are propagating in a particular direction, signals arriving from the direction of interest are added coherently, while those from other directions do not add coherently or cancel. For real-time three-dimensional applications, separate electronic circuitry is necessary for each transducer element. Using conventional implementations, the resulting electronics rapidly become both bulky and costly as the number of elements increases. Traditionally, the cost, size, complexity and power requirements of a high-resolution beamformer have been avoided by "work-around" system approaches. For real-time three-dimensional high-resolution ultrasound imaging applications, an electronically steerable two-dimensional beamforming processor based on a delay-and-sum computing algorithm is chosen.

Figure 1:
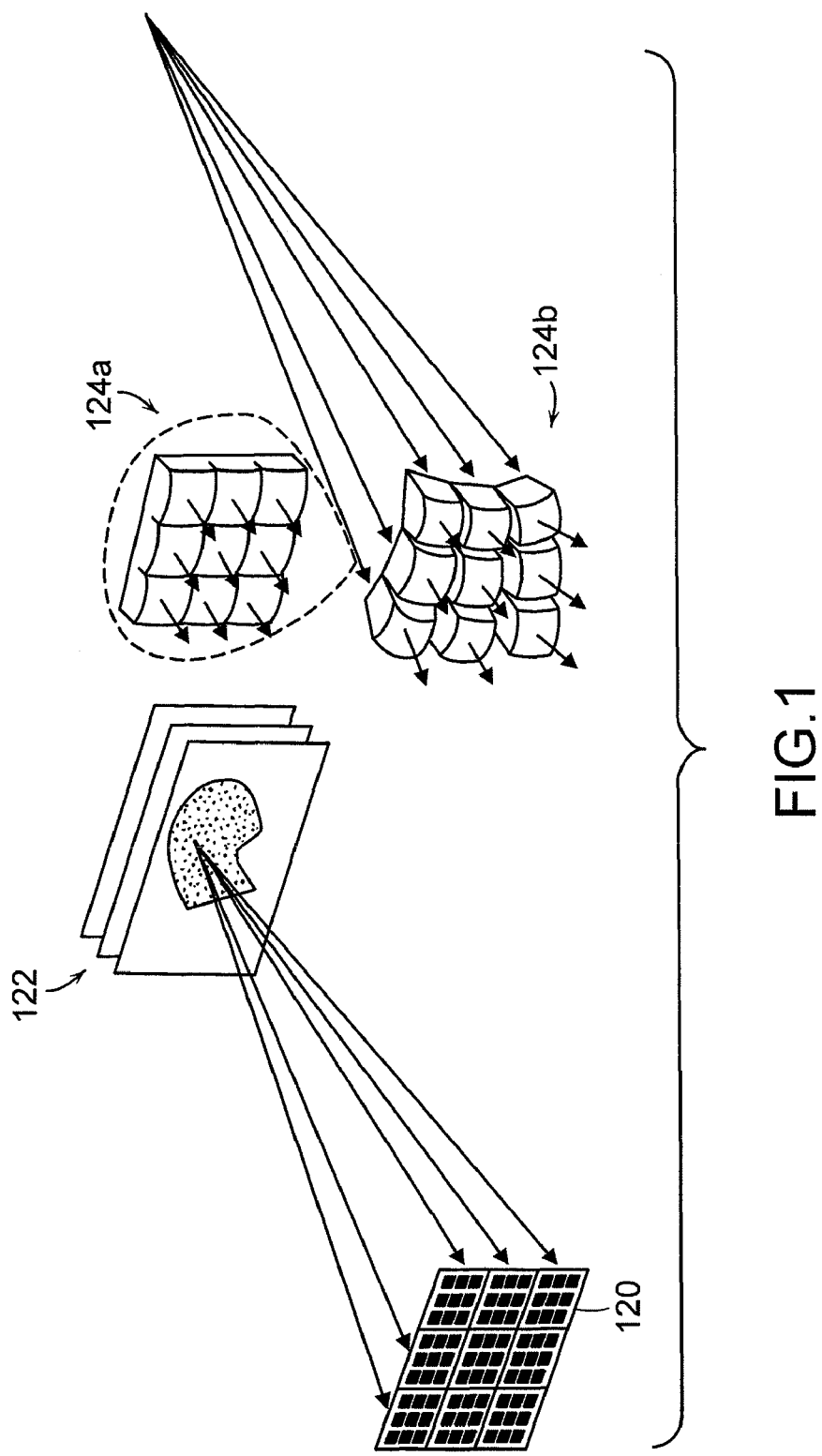
FIG. 1 illustrates the use of a two dimensional tiled array for ultrasound imaging in accordance with the invention.

The concept of an electronically-adjustable acoustic conformal lens is to divide the surface of a 2D transducer array into plane "tiles" of relatively small subarrays. As described in U.S. Pat. No. 6,292,433 the entire contents of which incorporated herein by reference, and illustrated in FIG. 1 the tiles/subarrays 120 are made small enough so that when an object is placed within the field-of-view of the imaging system, the incident radiation 122 from the object toward each "tile" can be treated using a far-field approximation. Additional delay elements are incorporated as second-stage processing to allow all subarrays to be coherently summed (i.e., global near-field beamforming can be achieved by simply delaying and then summing the outputs from all subarrays.) The delay-and-sum beamformer allows each subarray to "look" for signals radiating from a particular direction. By adjusting the delays associated with each element of the array, the array's look direction can be electronically steered toward the source of radiation. Thus instead of looking in one direction as seen at 124a, the direction of tiles 120 can be steered in different direction 124b. The delay line requirement for each element in the sub-array can be less than a hundred stages. Only long delays for global summing are needed for the final near field focusing.

Figure 2:
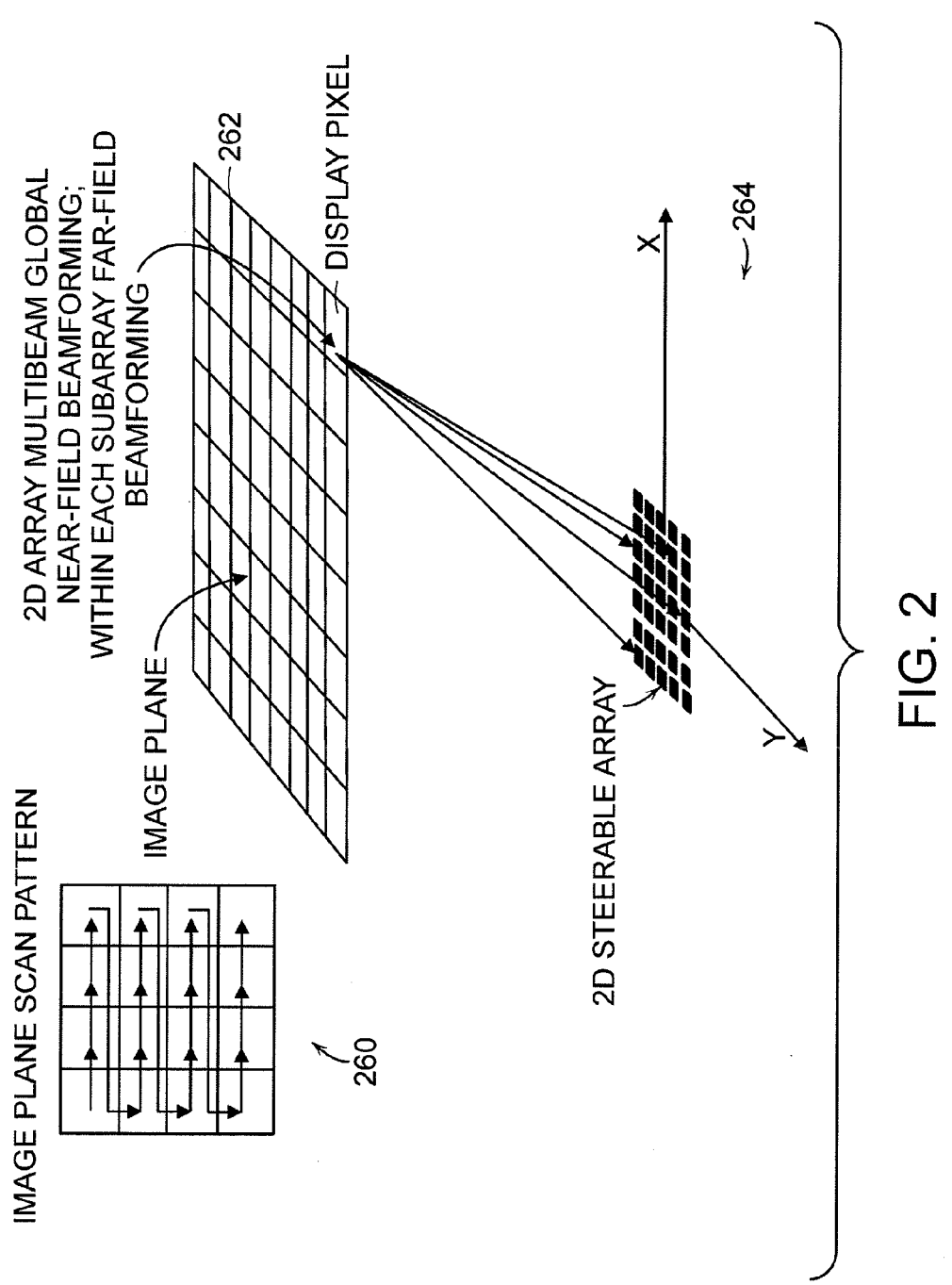
FIG. 2 illustrates a steerable two dimensional array in accordance with the invention.

To scan an image plane using a steerable beamformer system a process such as that shown in FIG. 2 can be used. A raster scan 260 can be used to scan an image plane 262 using a 2D steerable transducer array 264.

Figure 3A:
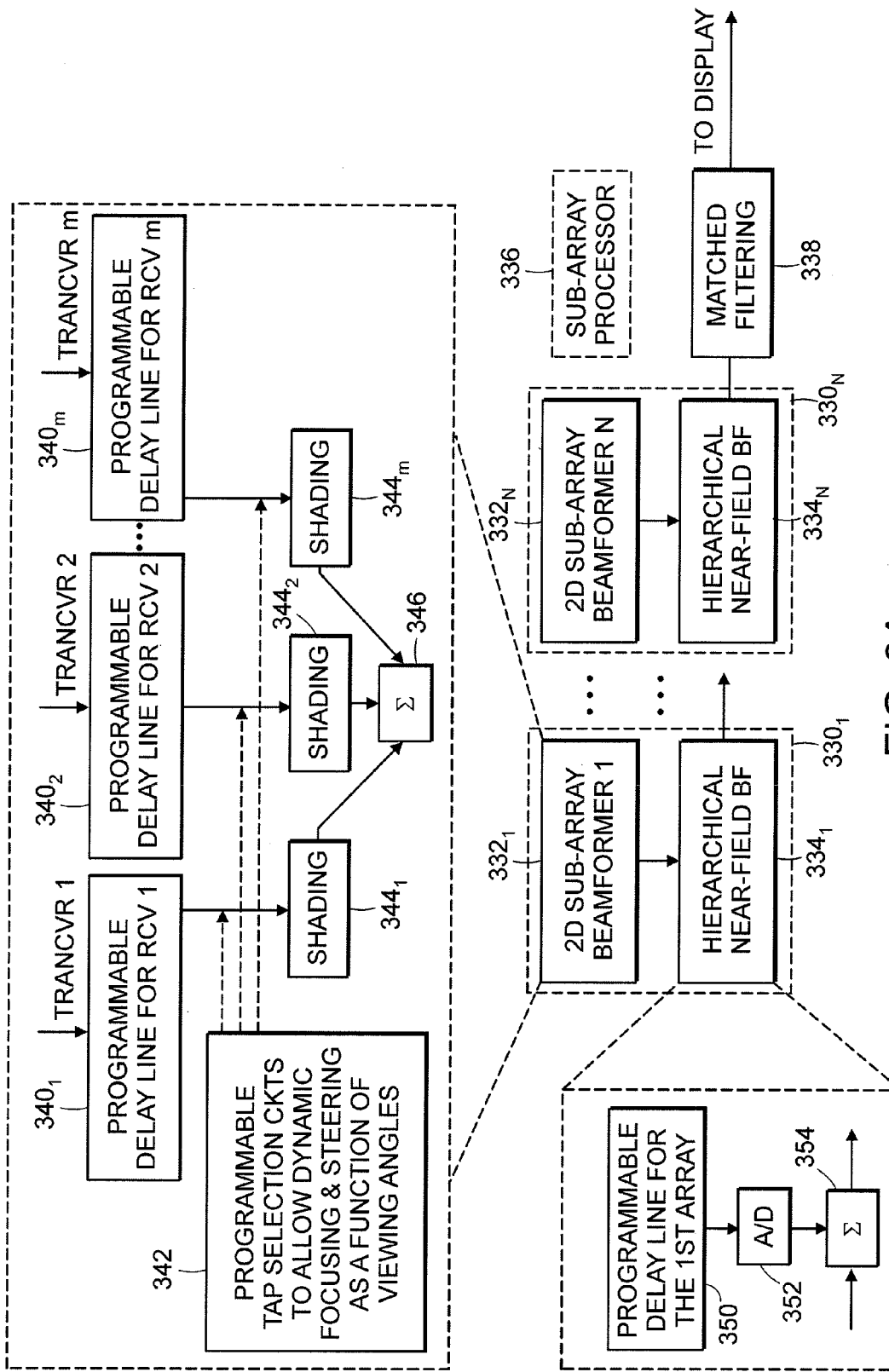
FIG. 3A illustrates the use of a first beamformer device for far field beamsteering and focusing and a second time delay beamformer for near field beamforming.
Figure 3B:
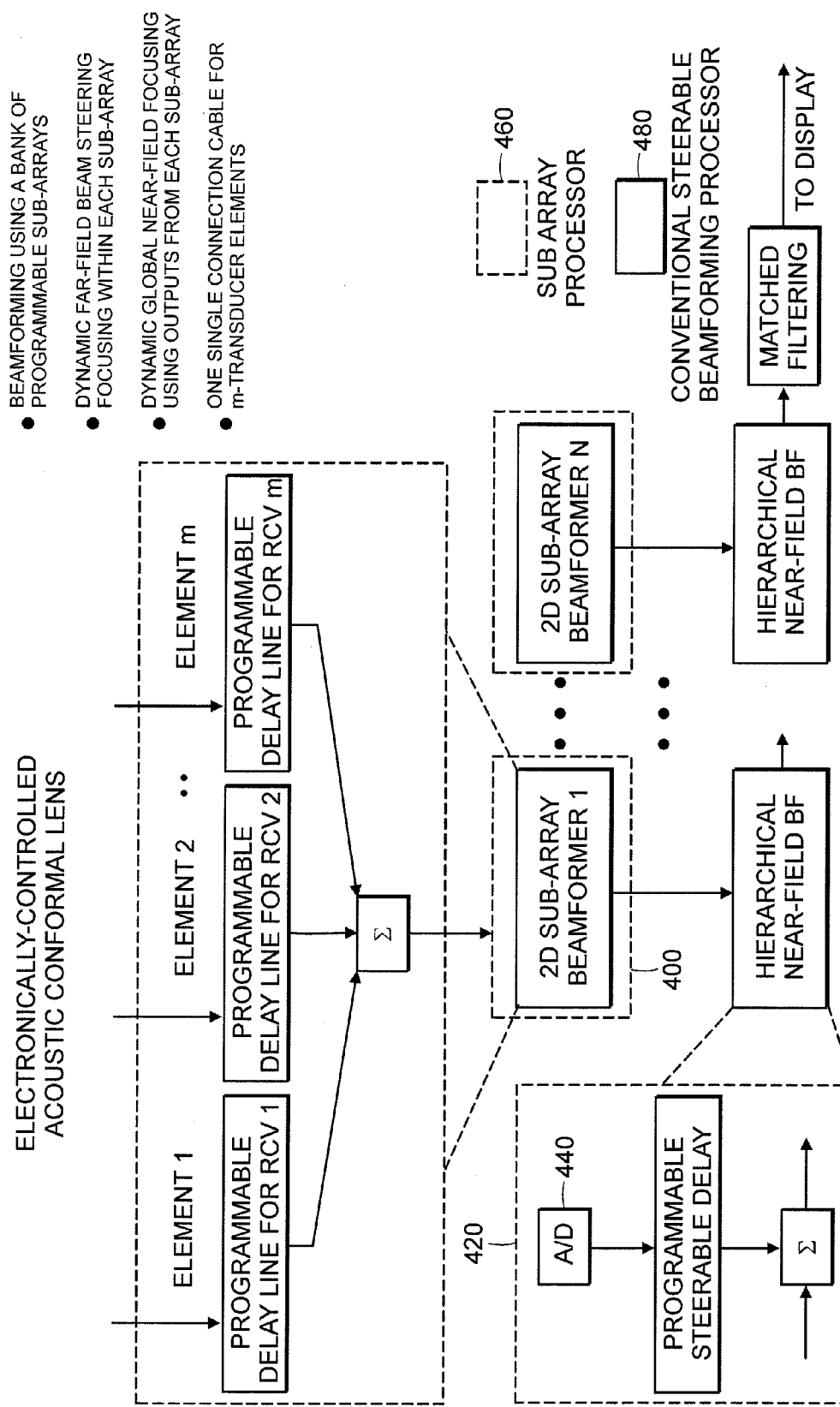
FIG. 3B illustrates a first analog subarray beamformer forwarding data to a digital beamformer near field beamformer.

A detailed diagram of an electronically-controlled beamforming system in accordance with the invention is shown in FIG. 3A. This system consists of a bank of parallel time-delay beamforming processors 330, 330N. Each processor 330 consists of two components: a 2D sub-array beamformer 332 for far-field beamsteering/focusing and an additional time delay processor 334 to allow hierarchical near-field beamforming of outputs from each corresponding subarray. The sub-arrays 332 include m-programmable delay lines 340 with tap selectors 342, multiplexers 344 and summed 346 output. As can be seen in FIG. 3A, for a system with n-sub-arrays, n-parallel programmable $2^{nd}$-stage near field time delays are needed for individual delay adjustment which are converted with A/D converter 352 to allow all n-parallel outputs be summed 354 coherently, in turn, this summed output is filtered 338 and provides the 3D images of the targeted object. A processor 336 controls sub-array operation. Use of the scan head with a second stage digital beamformer is shown in FIG. 3B. In this embodiment, a plurality of N sub-array beamformers 400 each receive signals from m transducer elements that have separate delay lines whose outputs are summed and provided to near-field beamformers 420 so that this beamformer can be a conventional system with conventional processor 480. A separate sub-array processor 460 controls beamformers 400.

Without using this hierarchical subarray far-field and then near-field beamforming approach, for an 80×80 element 2D array, a cable consisting of six thousand and four hundred wires is needed to connect the transducer array to a conventional beamforming system. As shown in FIG. 3A, the number of inputs to each subarray processor equals the total number of delay elements in the subarray, each sub-array only has a single output. The number of inputs to the subarray bank equals the number of 2D array elements, and the number of outputs from the subarray bank equals to the total transducer array element number divided by the subarray element number, i.e., the number of outputs from the subarray bank reference to the number of inputs is reduced by a factor equal to the size of the subarray. For example, if one selects to use a 5×5 subarray to implement this hierarchical beamforming concept, after the first stage subarray beamforming, the total number of wires needed to connect to the $2^{nd}$ stage near-field beamforming is reduced by a factor of 25. More specifically, as mentioned above, without using this 2D subarray beamforming, 6400 wires are needed to connect an 80×80-el 2D transducer array to a conventional back-end beamforming. Using a 5×5 subarray processing bank first, the number of wires required to connect to the backend beamforming system is reduced to 256. Based on the current invention, a bank of 256 5×5 element subarrays Beamformer can be integrated with a 80×80 element 2D array in the scan head, so a cable consisting of 256 wires is adequate to connect the integrated scan head with the back-end near-field beamforming system. It is important to note that 5×5 subarray far-field beamforming processors can be easily integrated in a small size Si integration circuit, eight of such 5×5 subarray beamforming can be integrated on one chip. Only 32 chips integrated into the scan head, it can reduce the cable size from 6,400 wires down to 256 wires.

Figure 4:
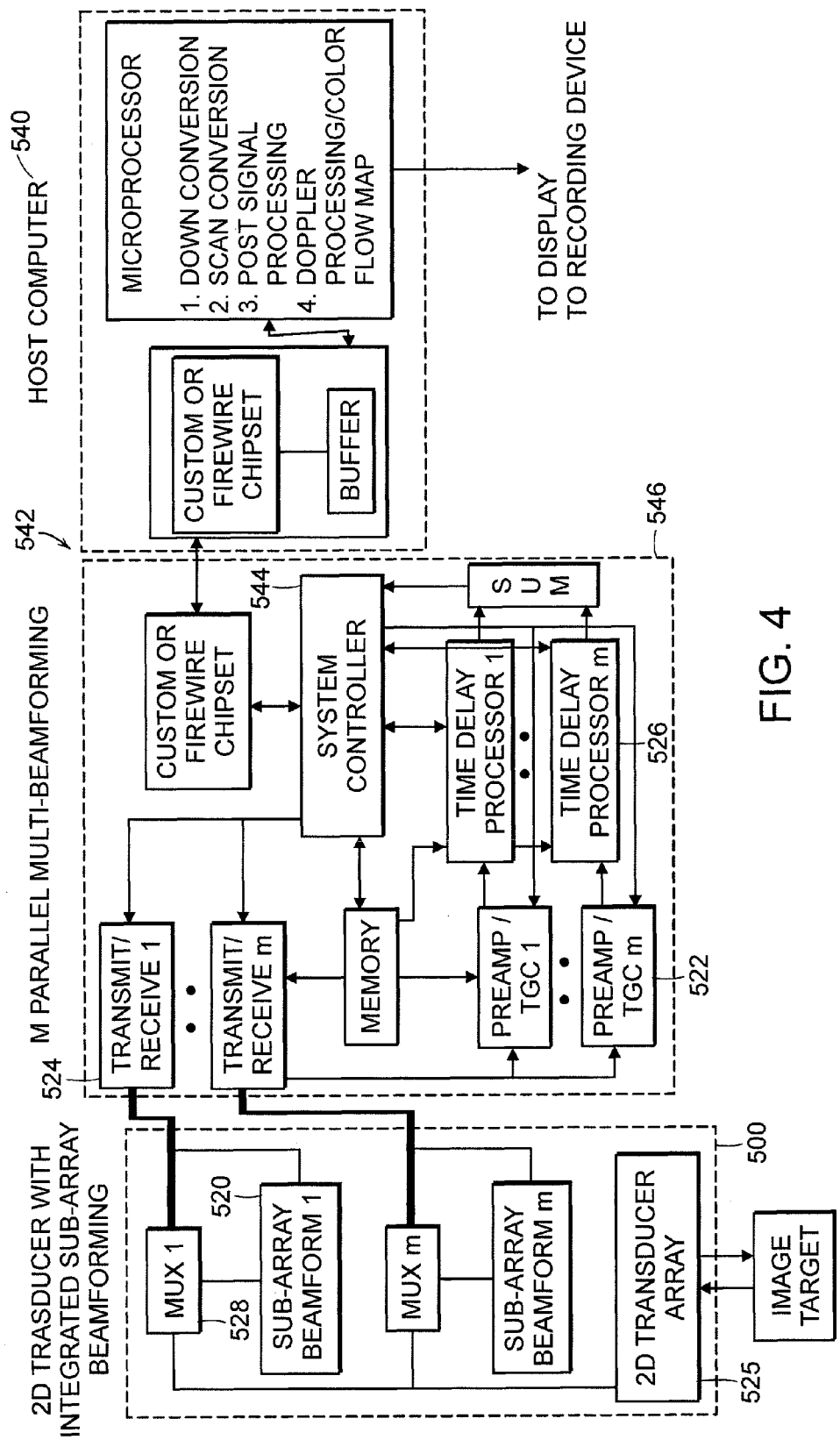
FIG. 4 illustrates a preferred embodiment of a three dimensional imaging system in accordance with the integrated Subarray scan head invention.
Figure 5:
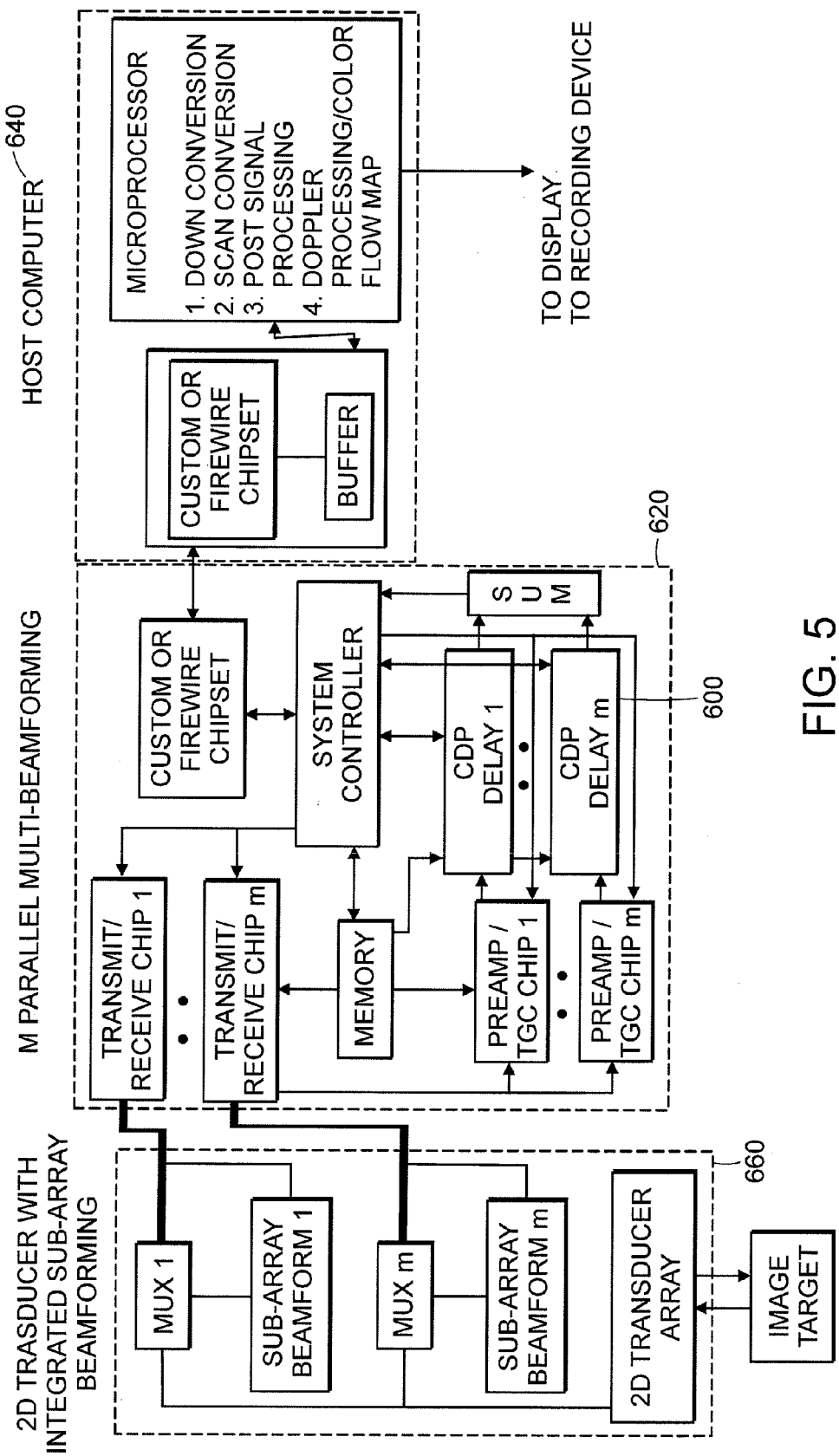
FIG. 5 illustrates a preferred embodiment of the integrated Subarray scan head invention using a charge domain processor for the $2^{nd}$ time delay beamforming.
Figure 6A:
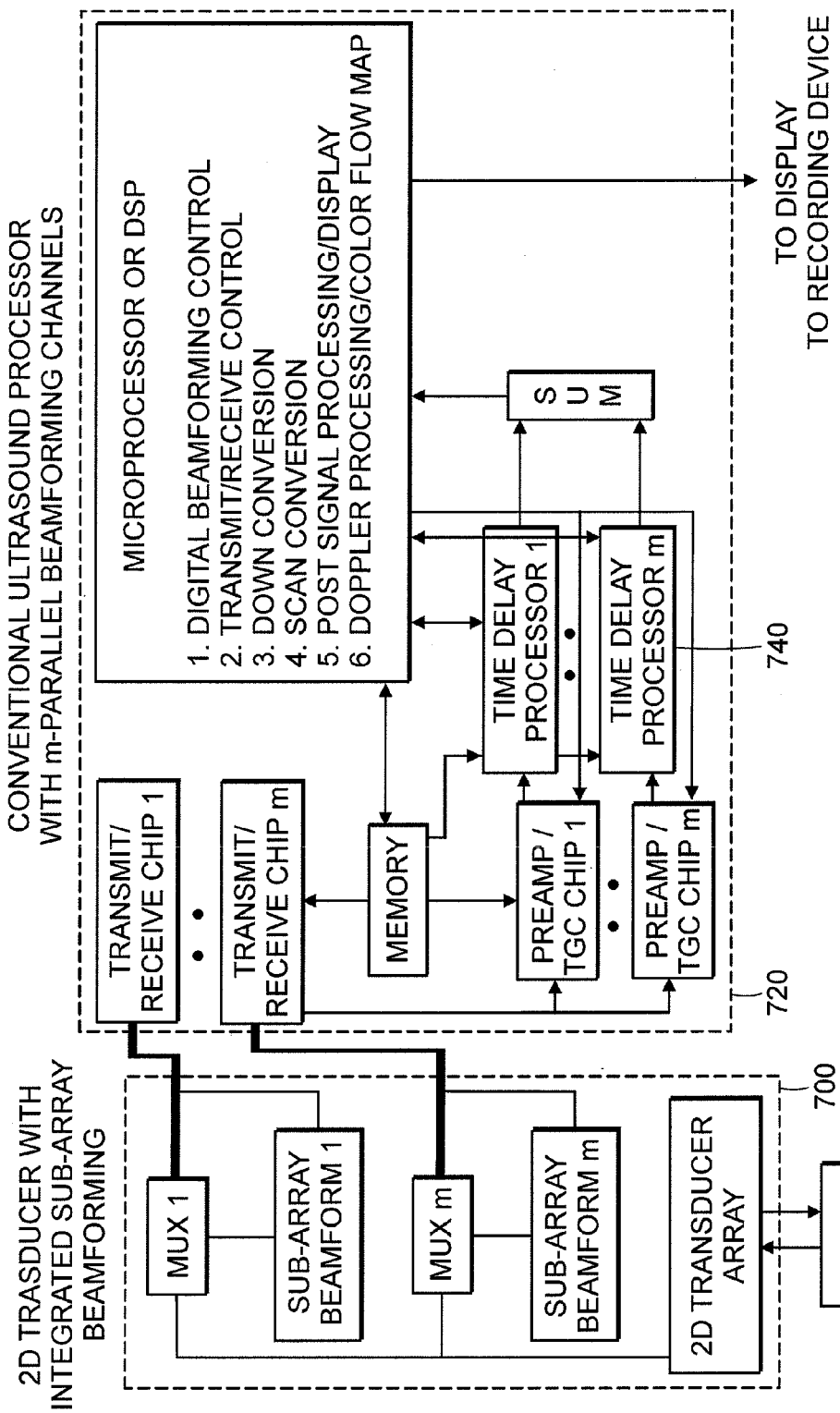
FIG. 6A illustrates the use of the integrated subarray scan head probe of the present invention with a second stage beamforming ultrasound processor.
Figure 6B:
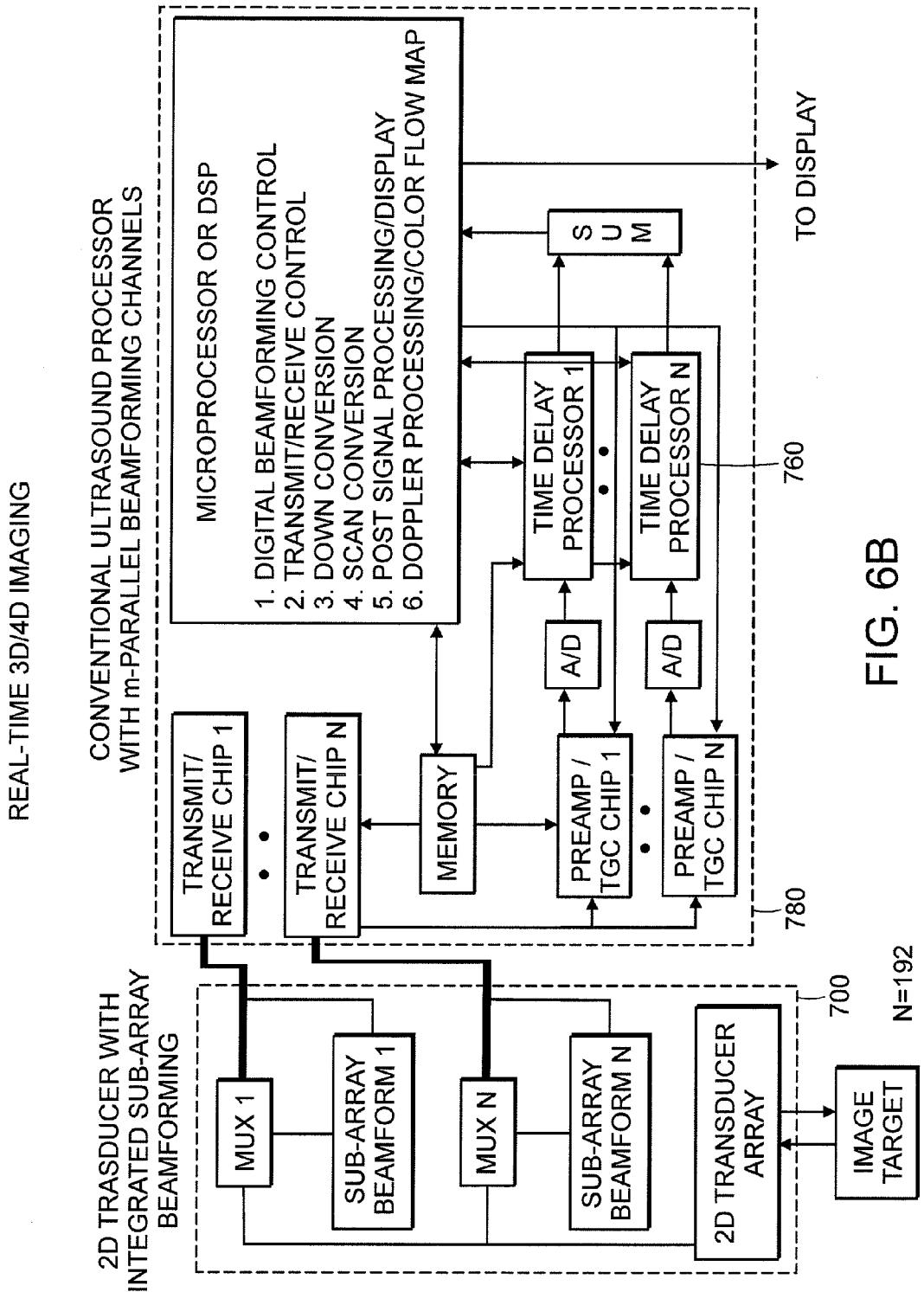
FIG. 6B illustrates use of the integrated Subarray scan head with a digital beamforming processor.

A preferred embodiment of the invention for a 2D array beamforming, each minimizing noise and cable loss with improved S/N performance, are described in FIGS. 4, 5 and 6. In all three implementations, the bank of m parallel subarray beamforming processors 520 and multiplexers 528 are integrated with the 2D transducer array 525 to create a compact, low-noise, scan head 500. FIG. 4 depicts a system that the compact scan head is connected to a dedicated processing module, in which the m-parallel preamp/TGCs 522 transmit/received chips 524 and the $2^{nd}$ stage time delay processing units 526 are housed. This dedicated processing module communicates with a host computer 540 via FireWire or USB or PCI bus 542. Control and synchronization is performed by the system controller 544 located in the processing module or housing 546. FIG. 5 depicts the same architecture as stated in FIG. 4, except, inside the dedicated processing module, the $2^{nd}$ stage time delay processing units are specifically implemented by using charge-domain programmable (CDP) time-delay lines 600 in housing 620 that is connected to handheld probe 660 and computer housing 648. FIG. 6B depicts a system that the compact sparse array scan head 700 is connected to a conventional, commercially available time-domain digital ultrasound imaging system 700 with n-parallel beamforming channels 760. It is easy to see that in FIG. 6A, the time-delay processor 720 can also be implemented by using CDP time-delay lines 740. In these embodiments the near-field beamforming is housed 720, 780 in the same housing with other image processing functions.

Figure 7:
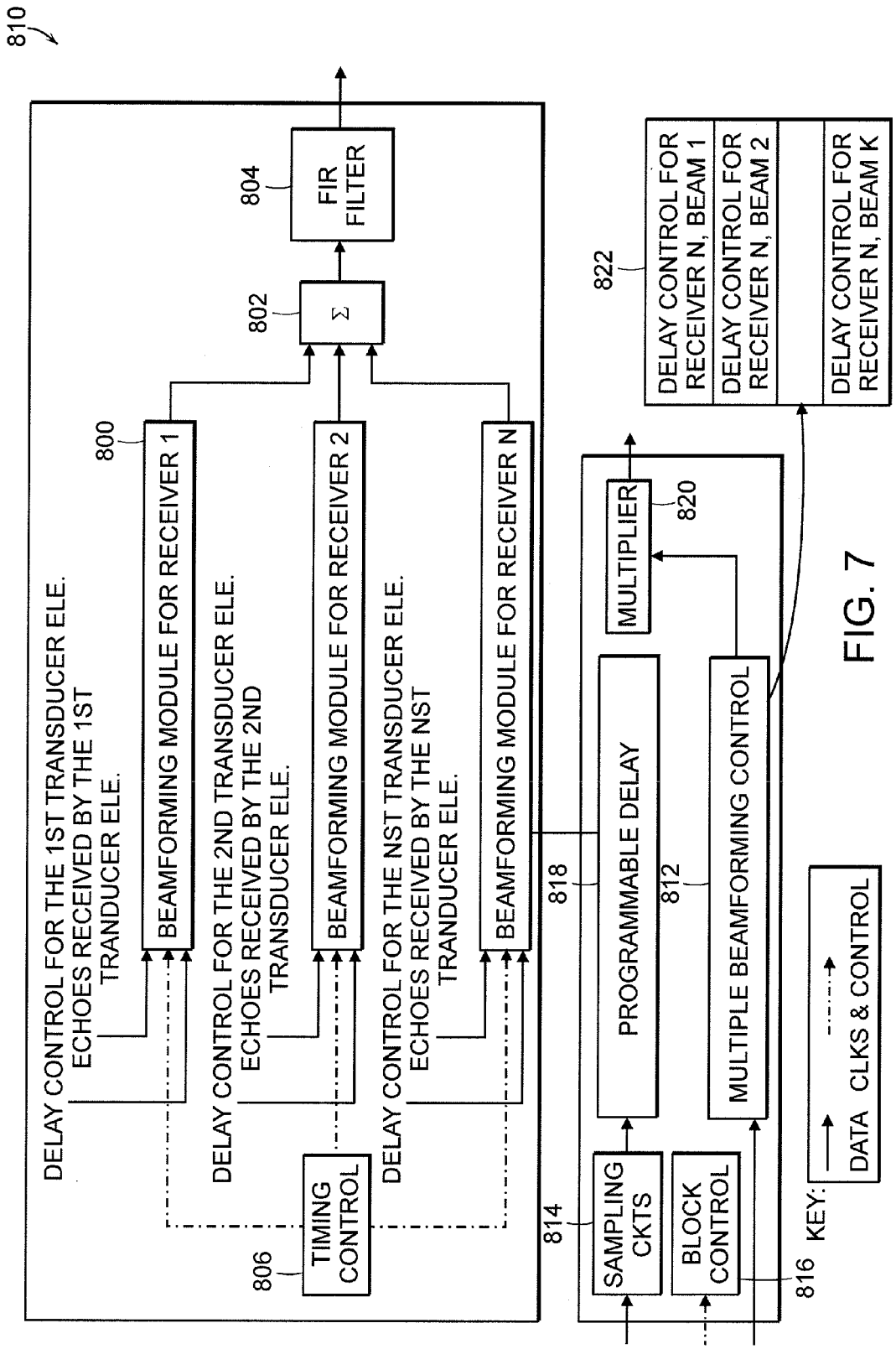
FIG. 7 illustrates an ultrasound system in accordance with the invention.

By systematically varying beamformer delays and shading along a viewing angle of a 2D transducer array, returned echoes along the line of sight representing the 3D radiation sources can be used to create the scanned image at the scanned angle. The system can provide continuous real-time large area scanned images throughout a large field of view at 20 frames/s or more. At this frame rate, the system can be used to display continuous 3D images vs. time, thus providing 4D information of the scanned object. As shown in FIG. 7 a CDP beamforming chip 810, a time multiplexed computing structure can be used to generate multiple beams, i.e., for each transmit pulse, the bank of 2D subarray beamformers 818 and its corresponding $2^{nd}$ stage near-field time-delay line are capable of providing multiple beams sequentially. The computing circuits sequentially generate the delays required for forming K beams. The device operates as follows. Once a set of sampled returned-echoes are loaded in the delay lines with sampling circuits 814, at time $t_1$, the delays required for forming beam 1 are computed 812 within each module 822 and applied in parallel to all delay lines. The sampled return-echoes with proper delays are coherently summed 802 and filtered 804 to form the first beam. At time $t_2$, the delays required for forming beam 2 are computed within each module and applied in parallel to all delay lines. The sampled return-echoes with proper delays are coherently summed to form the second beam. The procedure repeats until the Kth beam is coherently formed.

For example, if a computing circuit with 16-serial addressable outputs is built in with the CDP subarray and the $2^{nd}$ stage time delay lines, for each transmit pulse, 16 beams or scan lines each along a different scan angle can be created. For 256-pulses with a down-range depth of 15 cm, the system can generate a 4096-beams with a 64×64 pixel resolution at a frame rate of 20 frames/s. The system is fully programmable; the beamforming electronics can be adjusted to zoom-in to a smaller field-of-view for high-resolution or higher frame rate images. For example, using 192-transmit pulses with the same down-range depth of 15 cm, the system can generate a 3072-beams with a 64×48 pixel resolution at a 30 frame/s frame rate.

The array described addresses ultrasound imaging applications using a two-dimensional 2 cm×2 cm array at a frequency of 3 MHZ. The need for resolution on the order of less than half the wavelength dictates as large an aperture as possible that can be housed within a compact package. To interrogate a 90 degree scanning volume and also minimize the impact of grating lobes, an element pitch or separation of less than 0.25 mm is desirable, leading to a 80×80 element array. Using the subarray processing technique described above, a scan head with integrated subarray beamforming circuits followed by a $2^{nd}$ stage near-field beamsteering/beamfocusing system provides a practical implementation. However, the implementation still requires at least 32 subarray chips to be integrated on a scan head. An alternative pseudo random array design approach can be used to achieve this resolution with a much less amount of processing components in the scanned head.

To make a sparse array practical, the combination of low insertion loss and wide bandwidth performance is important for realizing acceptable imaging performance with low illumination levels. Quarter-wave matching layers with low acoustic impedance, but physically solid backing results in a robust array that loses only 3-4 dB in the conversion of received signal energy to electrical energy. Array bandwidths of 75% or more are typical of this design and construction process. Also, the transducer array employs element positioning and an interconnect system suitable for the beamformer circuitry. The electronics are mounted on printed-circuit boards that are attached to the transducer elements via flexible cables. In practice, a majority of the array elements are connected to outputs using the flexible cables. However, only a small fraction of the total number of elements are wired to the circuit boards. Nevertheless, the large number of array element connections are sufficient to insure a unique pattern of active-element locations in the final array.

As an example of a sparse array, assuming a 2×2 cm array with 256 active elements, the resulting filling factor is 4%. The output signal to noise ratio of the array is proportional to the number of active elements, so this filling factor corresponds to a loss in sensitivity of −13 dB when compared to a filled array of the same dimensions. To compensate for this loss, a transmitted signal of wider bandwidth is chosen to increase array sensitivity. In the approach presented here, the sensitivity is increased on the order of 10 dB. Further details regarding sparse array devices can be found in U.S. Pat. No. 6,721,235, the contents of which is incorporated herein by reference.

Figure 8A:
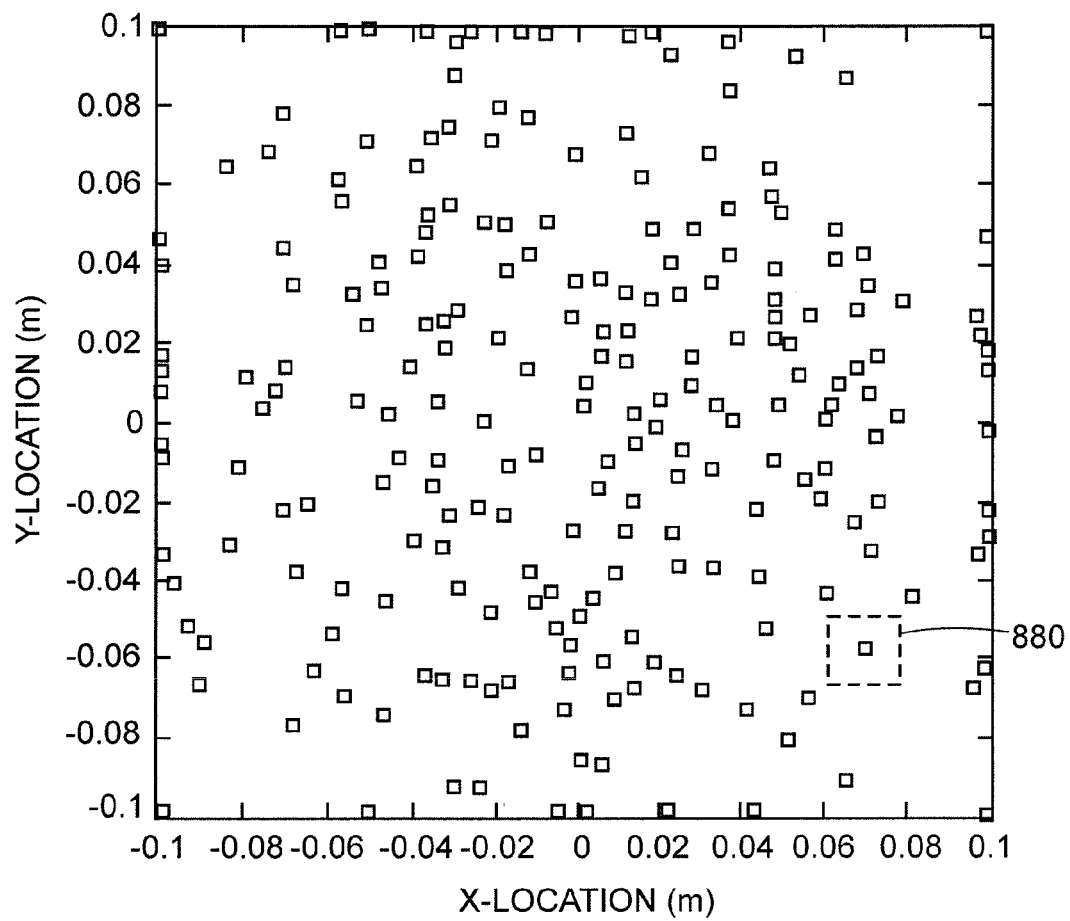
FIG. 8A illustrates a sparse array used in accordance with the invention.

Positioning the elements of the array follows the approach in which care must be taken to eliminate any periodicity that would produce grating lobes that compete with the main lobe. Pseudorandom or random arrays can be used (FIG. 8A). The geometry of activated element placement has been developed to maximize the efficiency of the beamformers while minimizing grating and side lobe clutter. Switching between a plurality of different array patterns is used to provide the most efficient beam pattern at different beam angles relative to the region or volume of interest being scanned. Thus, a first pattern can utilize that illustrated in FIG. 8A, which is than switched to a second pattern for a different scan angle. This can involve selecting a transducer element within a neighborhood 880 surrounding a given element to scan at a second angle.

The primary goal of the optimization method is to minimize the average side lobe energy. Specifically, this is done by interactively evaluating the optimization criterion:

$$J = \frac{1}{2u_{mx}^2} \int \int_S W(u_x, u_y) B(u_x, u_y) d u_x d u_y, \quad (1)$$

where the weighting function, $W(u_x, u_y)$, applies more weight to regions in the array response that require side lobe reduction. The optimization method begins with no weighting (i.e., $W(u_x, u_y)=1$) and proceeds by choosing successively better weighting functions that satisfy the optimization criterion. Since the side lobes that require the greatest reduction are related to the previously computed beampattern, $B(u_x, u_y)$, the weighting is chosen such that $W(u_x, u_y)=B(u_x, u_y)$. This is done in an interactive manner until convergence.

Basically, a random array is capable of producing an imaging point spread function that has a main lobe to average side lobe ratio of N, where N is the total number of active elements in the array. For the 256-element sparse array example, the resulting ratio is −13 dB. Using a wide bandwidth approach improves this ratio by 10 dB. Based on the preceding optimization criterion, a pseudorandom placement of the array elements was generated (FIG. 8A).

Figure 8B:
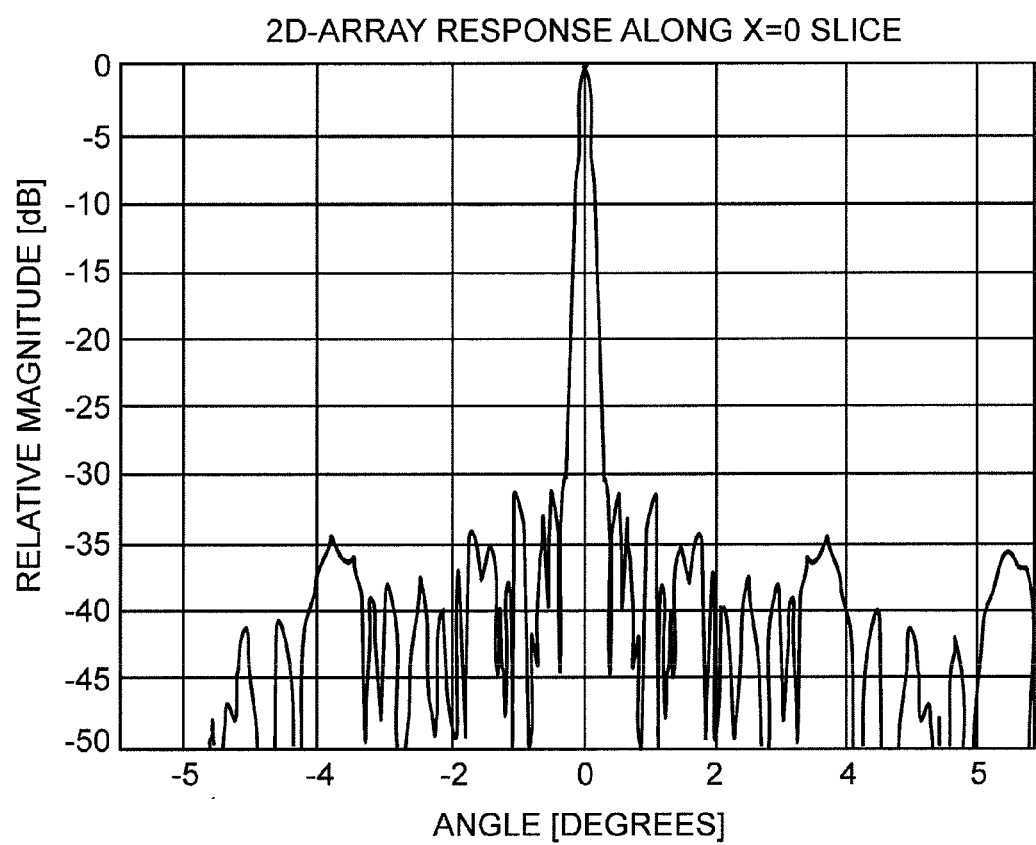
FIG. 8B graphically illustrates the sparse array performance.

FIG. 8B is a plot of the array performance, sensitivity versus cross range, for a 256-element sparsely-sampled array at 3 MHZ. The peak to maximum side lobe level is approximately 30 dB. To improve this performance, the system is configured to achieve the maximum main lobe to clutter level ratio possible, which has been independently verified.

Figure 9A:
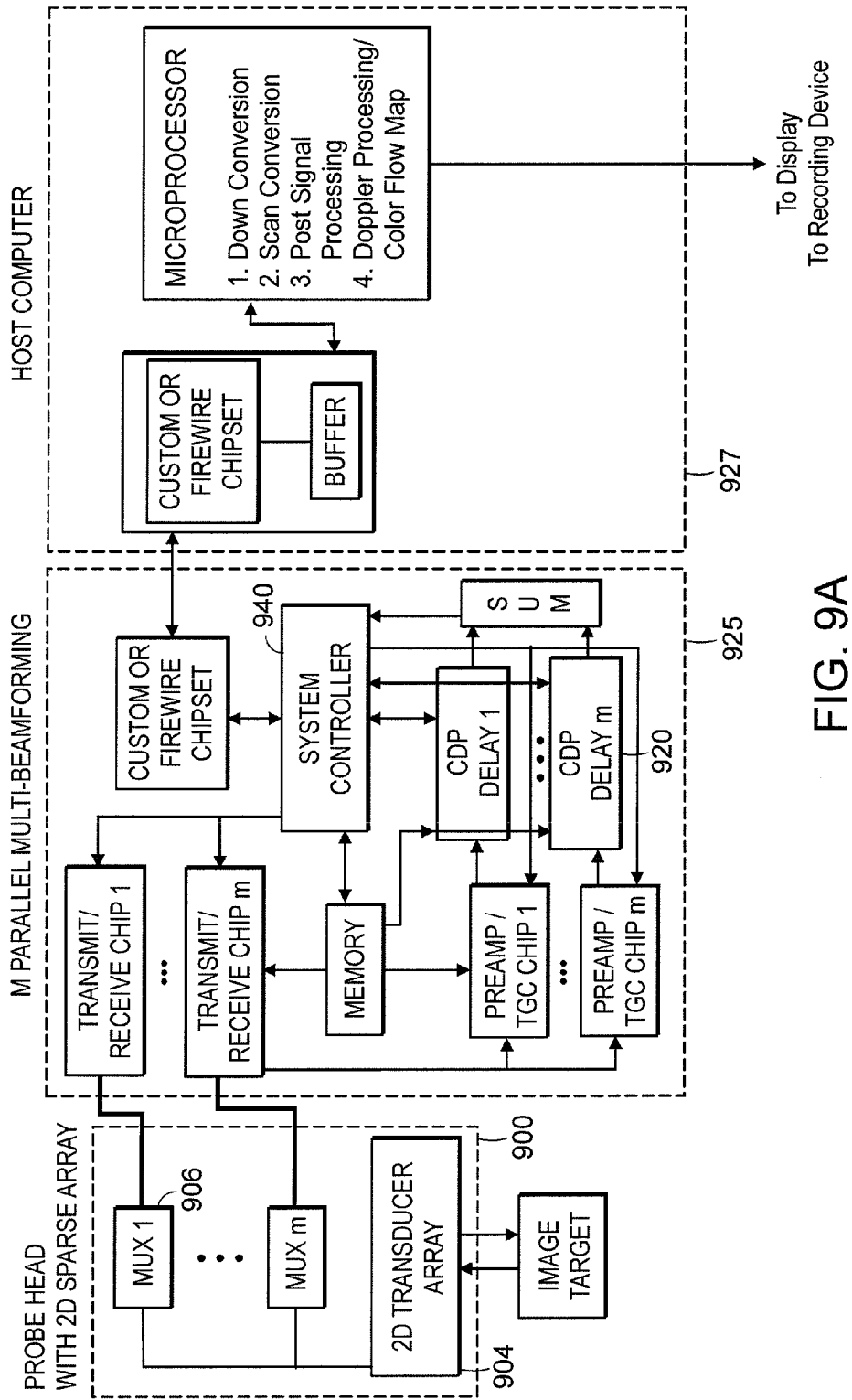
FIG. 9A illustrates the use of the integrated sparse array scan head probe of the present invention connected to a host system with charge-domain beamforming processing
Figure 9B:
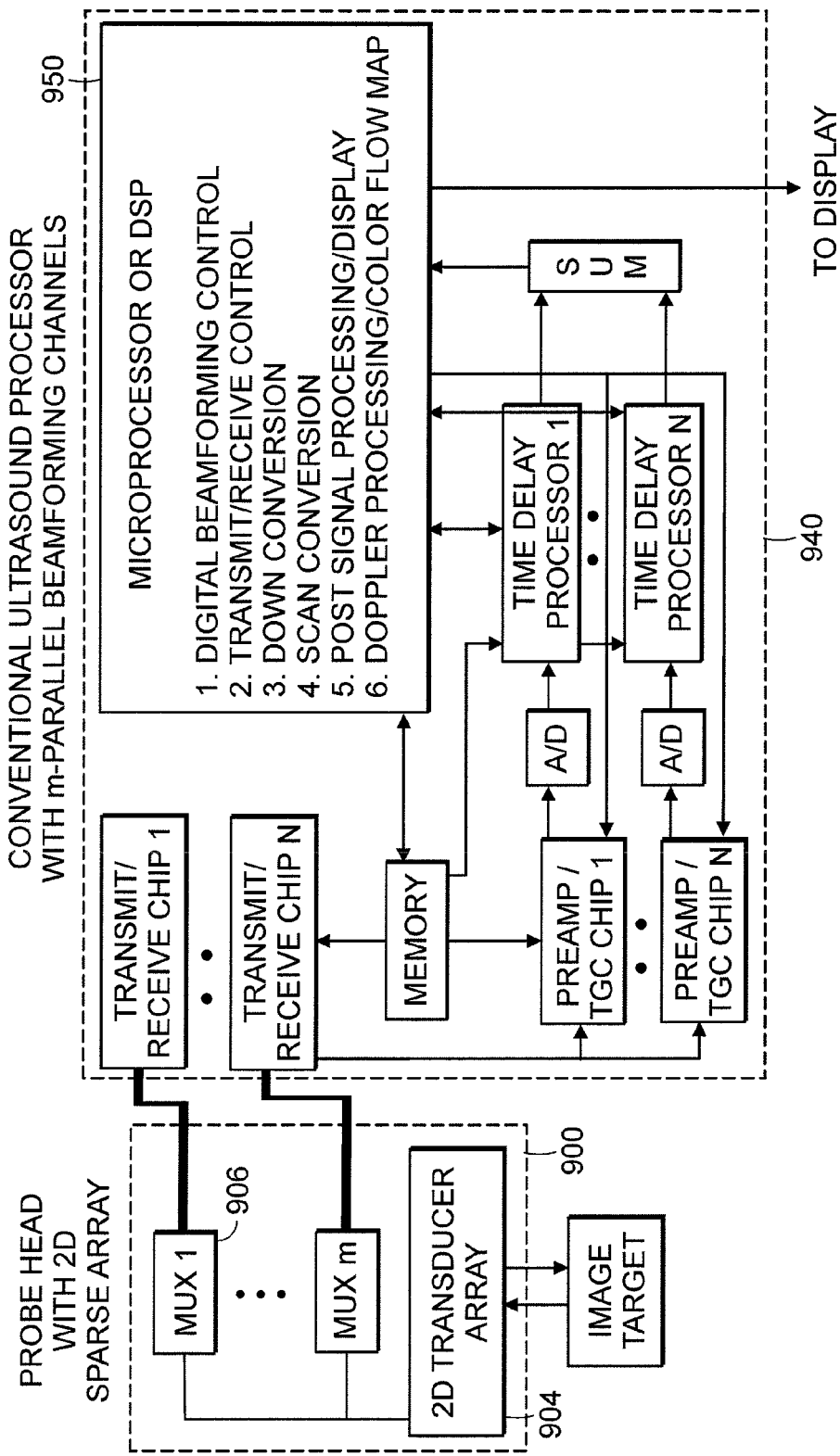
FIG. 9B illustrates the use of the integrated sparse array scan head probe of the present invention connected to a conventional digital ultrasound system with m-parallel beamforming components.

FIG. 9B depicts a system that the sparse array scan head 900 is connected to a conventional, commercially available time-domain digital ultrasound imaging system 940 with m-parallel beamforming channels. It is easy to see that in FIG. 9A, the time-delay processor can also be implemented by using CDP time-delay lines 920 in housing 925 that is connected to a separate computer 927. An array of m multiplexers 906 is used to switch between a sequence of scan patterns executed using a software program and system controller 940 or processor 950. The sequence of sparse array patterns is thus selected to scan at different scan angles of an object being imaged to provide 3D ultrasound imaging thereof.

A commercially available window-based 3D visualization software can be used to visualizing, manipulating, and analyzing the 3D multiple-beams volume image data generated by the electronically-adjustable acoustic conformal lens system. Traditionally, a clinician with 2D ultrasound images for diagnosis would look at the 2D scanned images slice by slice and mentally reconstruct the information into a 3D representation to judge the anatomy of the patient. This procedure requires the clinician to have well-founded experience as well as a highly sophisticated understanding of human anatomy. To create a "complete" image to the 3D structures, the clinician has to take all available slices into account. Looking at hundreds of slices is too time-consuming, even for a single patient. 3D visualization based on 3D volume data can help overcome this problem by providing the clinician with a 3D representation of the patient's anatomy reconstructed from the set of multiple-scanned beamforming data.

A commercially available software tool such as KB-Vol3D of KB-VIS technologies, Chennai, India, provides display or viewing 3D features such as:

Fast Volume-Rendering
Shaded Surface Display
Shaded-Surface module allows easy visualization of surfaces in the volume. Surfaces may be created by intensity-based thresholding. Alternatively, the Seeding option allows selection of specific connected structures of interest.
MIP (Maximum Intensity Projection) with Radials
MPR (Multiple-Plane-Reformating) with Oblique & Double-Oblique and 3D correlation
MRP Slabs & Multi-Cuts
Curved MPR
Color & Opacity Presets with Editor
Region-Growing and Volume Measurements
Cutaway Viewing with Slab-Volume and Interactive Real-time VOI
Volume-interiors are easily visualized using the "Cutaway-Viewing" tool. A Cut-Plane is used to slice through the volume, revealing the interior regions. The cut-plane is easily positioned and oriented using the mouse.

The VOI (Volume-of-Interest) tool allows interactive, real-time Volume-of-Interest display. The user can isolate and view sub-volumes of interest very easily and in real-time, using easy click-and-drag mouse operation.
Image Save in Multiple Formats
Images displayed by KB-Vol3D can be captured to various image formats (including DICOM, JPEG, and BMP etc.)
Movie Capture in AVI Format
Visualization operations can also be captured to an AVI movie .le and played on Windows Media Player, QuickTime, and Real Player etc.

Figure 10:
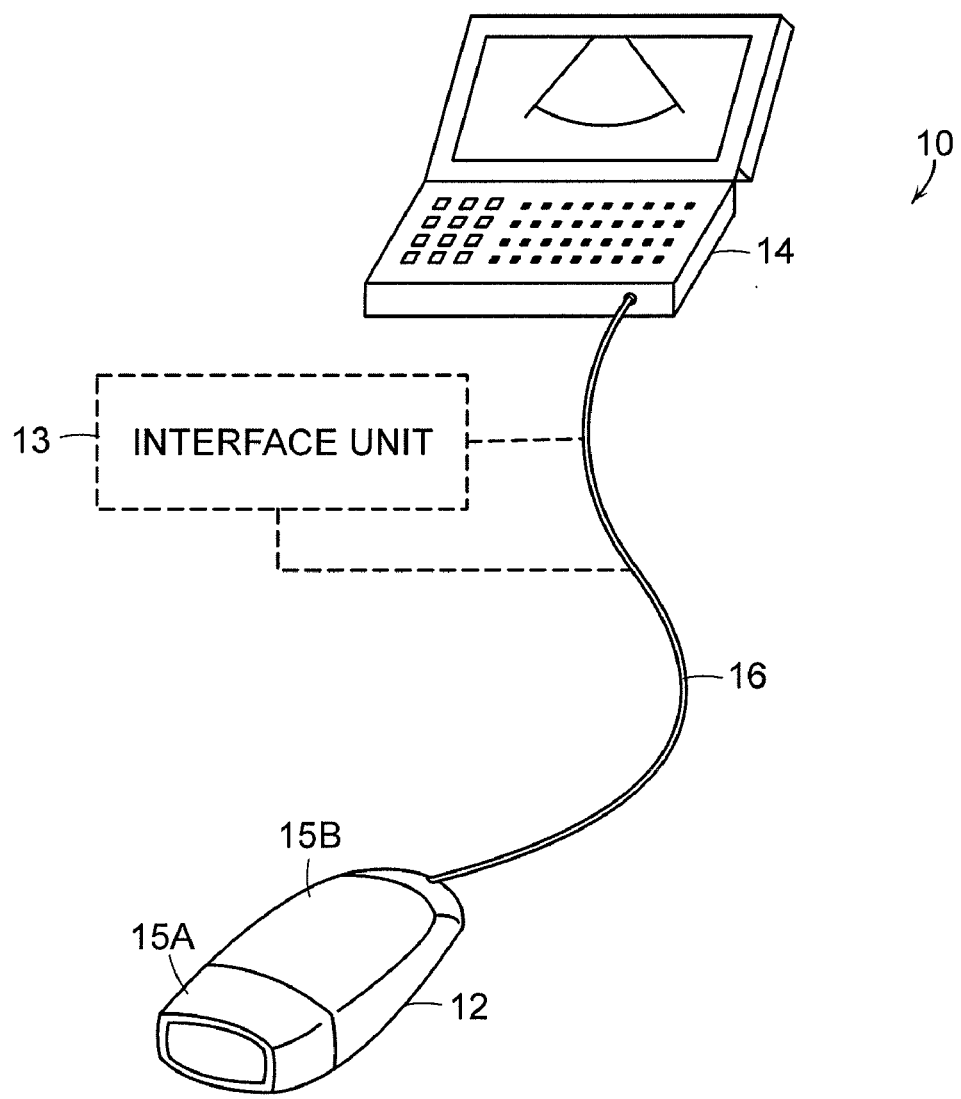
FIG. 10 illustrates a scan head connected to a portable computer in accordance with a preferred embodiment of the invention.

The invention can be implemented using a scan head 12 connected to a portable computer 14 as shown in FIG. 10. the ultrasound system 10 can also include a cable 16 to connect the probe 12 to the processor housing 14. Certain embodiments can employ an interface unit 13 which can include a beamformer device. Scan head 12 can include a transducer array 15A (2D) and a circuit housing 15B which can house multiplexer and/or beamforming components as described in detail in U.S. Pat. Nos. 6,106,472 and 6,869,401, the entire contents being incorporated herein by reference.

The claims should not be read as limited to the recited order or elements unless stated to that effect. All embodiments that come within the scope and spirit of the following claims and equivalents thereto are claimed as the invention.

What is claimed is:

1. A medical ultrasound imaging system comprising:
a two dimensional (2D) array of transducer elements in a probe housing, the array of transducer elements having a plurality of 2D transducer sub-arrays;
a first beamformer device in the probe housing, the first beamformer device having a plurality of sub-array beamformer elements that receive signals from the plurality of 2D transducer sub-arrays;
a multiplexer device in the probe housing, the multiplexer device having a plurality of multiplexer elements, each of the plurality of multiplexer elements being connected to one of the sub-array beamformer elements and such that each of the plurality of 2D transducer sub-arrays are each connected to one of the plurality of multiplexer elements;
a summing device for summing of a plurality of delayed signals within the probe housing;
a controller to sparsely actuate the plurality of 2D transducer subarrays to generate a plurality of scan lines at a plurality of different scan angles for each transmit pulse; and
a second beamformer device in a second housing, the second beamformer being in communication with the probe housing to receive summed beamformed data from the first beamformer device, the second housing including an image processor and a display.

2. The system of claim 1 wherein the first beamformer device comprises a plurality of beamformer elements and a corresponding plurality of multiplexer elements.

3. The system of claim 1 further comprising a processor housing having an image processor programmed to perform 3D image processing and Doppler processing.

4. The system of claim 3 wherein the second housing is connected to the probe housing with a first cable and is connected to the processor housing with a second cable.

5. The system of claim 1 wherein the two dimensional array has at least 256 elements.

6. The system of claim 1 wherein the first beamformer device comprises a plurality of beamforming channels that receives signals from a two dimensional sub-array having N×M transducer elements.

7. The system of claim 1 wherein the second beamformer device comprises a digital beamformer.

8. The system of claim 1 wherein the first beamformer device comprises a charge domain processor.

9. The system of claim 1 further comprising a processor programmed to actuate the system to collect at least 10 3D images per second.

10. The system of claim 1 wherein the system comprises a portable ultrasound system.

11. The system of claim 1 further comprising a plurality of transmit circuits in the second housing that are connected to the multiplexer device and a system controller connected to the transmit circuits such that the system controller actuates a plurality of sparse transmission array patterns of the array of transducer elements.

12. The system of claim 1 further comprising a transmit circuit that generates a transmit pulse actuating 16 separately steerable beams with the array of transducer elements.

13. A medical ultrasound scan head comprising:
a two dimensional (2D) array of transducer elements in a probe housing, the probe housing having a cable for connecting to a medical ultrasound processor;
a first beamformer device in the probe housing, the first beamformer device including a plurality of sub-array beamformer elements that receive signals from a corresponding plurality of 2D transducer sub-arrays; and
a multiplexing network in the probe housing, the multiplexing network having a plurality of multiplexer elements that are connected to the plurality of sub-array beamformer elements, each sub-array beamformer element connected to one of the plurality of 2D transducer sub-arrays.

14. The scan head of claim 13 wherein the two dimensional array comprises a sparse transmission array.

15. The scan head of claim 13 wherein the first beamformer device comprises a charge domain processor.

16. A medical ultrasound imaging system comprising:
a two dimensional array of transducer elements in a probe housing having a plurality of 2D transducer subarrays;
a plurality of multiplexer elements that switches the array between a plurality of sparse transmission array patterns;
a plurality of beamformer circuits in the probe housing, each beamformer circuit being connected to one of the multiplexer elements and one of the plurality of 2D transducer subarrays;
a portable processor housing connected to the probe housing with a cable, the portable processor housing including a display; and
a processor programmed to sparsely actuate the transducer array with a plurality of transmit circuits to transmit a plurality of pulses, each transmit pulse generating 16 separately steerable beams at different scan angles to generate at least 10 three dimensional images per second.

17. The system of claim 16 further comprising a processor housing connected to the probe housing, the processor housing having at least one image processor programmed to perform 3D image processing and Doppler processing and having a controller to sequentially actuate sparsely selected array elements.

18. The system of claim 16 wherein the two dimensional array comprises a sparse array having at least 256 transducer elements.

19. The system of claim 16 wherein the first transmission sparse array pattern transmits at a first scan angle and the second transmission sparse array pattern transmits at a second scan angle different from the first scan angle.

20. A medical ultrasound imaging system comprising:
a two dimensional array of transducer elements in a probe housing, the two dimensional array of transducer elements comprising a plurality of 2D transducer subarrays;
a multiplexing network in the probe housing to sparsely actuate the array elements that transmit a plurality of different sparse transmission patterns in sequence, the multiplexing network comprising a plurality of multiplexing elements connected to the corresponding plurality of 2D transducer subarrays;
a first beamformer in the probe housing that is connected to the multiplexing network, the first beamformer receiving signals from the array of transducer elements such that data are generated;
a second beamformer device in a second housing, the beamformer being in communication with the probe housing to receive summed data from the first beamformer device
a controller in the second housing in communication with the probe housing to sequentially actuate selected transducer elements to form the plurality of sparse transmission patterns; and
an image processor in the second housing.

21. The system of claim 20 further comprising a controller that activates a fully populated receiver transducer array.

22. The system of claim 20 further comprising a sub-array processor.

23. The system of claim 20 further comprising a steerable beamforming processor.

24. The scan head of claim 13 further comprising a plurality of sub-array processors.

* * * * *